United States Patent [19]
Ikariya et al.

[11] Patent Number: 5,869,739
[45] Date of Patent: Feb. 9, 1999

[54] METHOD FOR PRODUCING FORMIC ACID OR ITS DERIVATIVES

[75] Inventors: Takao Ikariya; Philip Gregory Jessop; Yi Hsiao; Ryoji Noyori, all of Aichi, Japan

[73] Assignees: Research Development Corporation of Japan; NKK Corporation, both of Tokyo, Japan

[21] Appl. No.: 754,249

[22] Filed: Nov. 20, 1996

Related U.S. Application Data

[62] Division of Ser. No. 334,157, Nov. 4, 1994, Pat. No. 5,639,910.

[30] Foreign Application Priority Data

| Nov. 4, 1993 | [JP] | Japan | 5-274721 |
| Jun. 7, 1994 | [JP] | Japan | 6-125401 |
| Jun. 7, 1994 | [JP] | Japan | 6-125402 |

[51] Int. Cl.[6] ............ C07C 69/02; C07C 67/00
[52] U.S. Cl. ............ 560/231; 560/239
[58] Field of Search ............ 560/231, 239

[56] References Cited

U.S. PATENT DOCUMENTS

| 4,855,469 | 8/1989 | Baile et al. | 562/609 |
| 5,198,589 | 3/1993 | Rathke et al. | 568/454 |
| 5,239,117 | 8/1993 | Nicholas et al. | 562/609 |

FOREIGN PATENT DOCUMENTS 0 094 785  11/1983  European Pat. Off. .

OTHER PUBLICATIONS

Research Development Corporation, "formic Acid Direct from Carbon Dioxide", *European Chemical News,* abstract, Mar. 1994.

Jessop et al., "Homogeneous Catalytic Hydrogenation of Supercritical Carbon Dioxide", *Nature,* Vol. 368, No. 6468, pp. 231–233, 17 Mar. 1994.

*Primary Examiner*—Gary Geist
*Assistant Examiner*—Rosalynd Keys
*Attorney, Agent, or Firm*—Wenderoth, Lind & Ponack, L.L.P.

[57] ABSTRACT

Formic acid or derivatives thereof are produced from non-toxic carbon dioxide in the supercritical state, using it as raw materials, without using solvents, and at a high efficiency owing to a high reaction velocity, by reacting said carbon dioxide and an active hydrogen group-containing compound.

5 Claims, 2 Drawing Sheets

METHOD FOR PRODUCING FORMIC ACID OR ITS DERIVATIVES

This is a divisional application of Ser. No. 08/334,157 filed Nov. 4, 1994 now U.s. Pat. No. 5,639,910.

FIELD OF THE INVENTION

The present invention relates to a method for producing formic acid or derivatives thereof. More specifically, the present invention relates to a novel method to produce formic acid or derivatives thereof, which are useful as raw materials, etc. in the organic chemical industry, by the reaction of carbon dioxide in the super critical state with an active hydrogen group-containing compound at a reaction velocity not attainable in the conventional liquid phase reaction.

PRIOR ART

Formic acid and their derivatives have been and are useful as basic raw materials, etc. in the organic chemical industry, and extensively used in various industrial sectors for the production of, for example, chemicals, plastics, pharmaceuticals, agricultural chemicals, etc.

Formic acid is conventionally produced from caustic soda and carbon monoxide, or from lime and carbon monoxide as raw materials.

The conventional methods use toxic carbon monoxide (CO) and thus are not favorable. A number of new production methods has been developed in an attempt to replace the conventional methods that use carbon monoxide. Actually, several methods to use carbon dioxide ($CO_2$) as raw materials, replacing carbon monoxide (CO), have been reported recently. These introduce a method to produce formic acid from carbon dioxide ($CO_2$) and hydrogen ($H_2$). These methods include, for example, (I) a method to produce formic acid by using magnesium formate with titanium tetrachloride, magnesium and tetrahydrofuran base as described in J. Organometal. Chem., 80 C27 (1974), (II) a method to produce formic acid from carbon dioxide and hydrogen in a benzene solvent in the presence of a palladium, ruthenium, iridium, or rhodium catalyst and an organic amine such as triethylamine as described in Chemistry Letters (1976), p863, (III) a method to produce formic acid from carbon dioxide and hydrogen in the presence of water and a metal salt using ruthenium catalyst as disclosed in the provisional Japanese patent application No. 56-140948, and (IV) a method to produce formic acid from carbon dioxide and hydrogen in a dimethylsulphoxide or water solvent using a rhodium complex in the presence of water and triethylamine as described in J. Chem. Soc. Commun. p623 (1992) and p1465 (1993).

These conventional known methods use, without exception, a large amount of solvents for reaction, and thus complicated procedures are required to separate formic acid as the reaction product, from catalysts and solvents. Further, all these methods do not have a sufficiently high reaction rate, and are thus not necessarily suitable for practical application.

For these reasons, people have been needing the development of a new formic acid production method which is simple to use, has excellent productivity and a fast reaction velocity.

Formic acid ester compounds as derivatives of formic acid are useful as basic raw materials, etc. in the organic chemical industry, and are extensively used in various industrial fields to produce, for example, chemicals, plastics, pharmaceuticals, agricultural chemicals, etc. Methyl formate as a product, in particular, can be isomerized in the presence of a catalyst to give acetic acids, and for this reason, a new acetic acid production method will be easily developed if methyl formate can be produced at a low cost.

Formic acid esters can be synthesized by esterification of formic acid and alcohols, and thus the production method using this esterification reaction has conventionally been known is a method to synthesize formic acid esters from toxic carbon monoxide and alcohols in the presence of a metal alkoxide catalyst. Other known methods, employ the reaction of carbon dioxide ($CO_2$), hydrogen ($H_2$), and an alcohol. Methods to produce formic acid esters compounds from $CO_2$, $H_2$ and alcohols are also known. These methods use, for example, a combination of transition metal complexes and boron fluoride (M. E. Vol'pin et al, Izv. Akad. Nauk SSSR, Ser, Khim, 1972, Vol. 10, p2329) or catalysts such as $[W(CO)_5(HCO_2)][N(P(C_6H_5)_3)_2]$ (P. J. Darensbourg et al. J. Am. Chem. Soc., 1984, Vol. 106, p3750), $[HFe(CO)]_{11}[N(P(C_6H_5)_3)_2]$ (G. O. Evans et al, Inorg. Chim. Acta, 1978, Vol. 31, pL387), $RuH_2[P(C_6H_5)_3]_4$ (Y. Inoue, H. Hashimoto et al, J. Chem. Soc., Chem. Commun., 1975, p718), $RuCl_2[P(C_6H_5)_3]_3/Al_2O_3$ (P. G. Lodge et al, EPA 0094785, 1983), $RhCl[P(C_6H_5)_3]_3$ (Y. Inoue, H. Hashimoto et al, J. Chem. Soc., Chem. Commun., 1975, p718, and N. Sugita et al, Bull. Inst. Chem. Res., Hyoto Univ., 1985, Vol. 63, p63), $Pd(dppe)_2$(dppe: diphenylphosphinomethane) (Y. Inoue, H. Hashimoto et al, J. Chem. Soc., Chem. Commun., 1975, p718), and $MnPd (CO)_3(dppm)_2Br$(dppm:diphenyl phosphinomethane) (B. F. Hoskins et al, Inorg. Chim. Acta, 1983, Vol. 77, pL69).

However, a large amount of solvents must be used in all of those known methods and thus complicated procedures are required to separate formic acid ester compounds as the reaction product, from the catalyst and solvents. Further, the reaction rate and the final yield of these known methods are not high enough and these methods are not necessarily suitable for practical application. Toxicity is always a problem in the methods that use carbon monoxide.

For these reasons, the development of a new method to produce formic acid ester compounds which is simple to use, has an excellent productivity and a fast reaction rate is needed.

Formamide derivatives of formic acid, are also useful as basic raw materials in the organic chemical industry. They are extensively used in various industrial fields of chemicals, plastics, pharmaceuticals, agricultural chemicals, etc. Among others, N, N-dimethylformamide (DMF) is widely used as a polar solvent for synthesis reactions.

Conventional methods to produce these formamides include (1) a method to react an amine and carbon monoxide at a high temperature and under a high pressure using metal alkoxide catalysts (DMF Dimethyl formamide chemical uses, E. I. du Pont de Nemours, 1967, p217). (2) a method to react an amine and methyl formates in the atmosphere of carbon monoxide using a metal alkoxide catalyst (DMF Dimethyl formamide chemical uses, E. I. du Pont de Nemours, 1967, p217), and (3) a general method of reaction of a carboxylic acid, and carboxylic acid derivatives such as a carboxylic acid anhydride, a halide, or carbamate of carboxylic acid with amines (described in The Chemistry of Amides, J. Zabiscky, or in EPA0 062 161 and DE2715044). Methods (1) and (2) above are used, for example, for the production of DMF for industrial use.

These conventional methods have their problems. For example, toxic carbon monoxide must be used at a high temperature and under a high pressure in the methods (1) and (2), or a high temperature is indispensable and the carboxylic acid derivatives, the main raw materials, must be separately synthesized in the methods (2) and (3).

Other known methods use less toxic carbon dioxide. In these methods, formamide derivatives are synthesized from carbon dioxide, hydrogen and an amine using metal complex catalysts. The catalysts used are 1) copper, zinc, cadmium, palladium or platinum halides or their phosphine or arsine complexes (U.S. Pat. No. 3,530,182), 2) phosphine complexes of cobalt, rhodium, iridium, and ruthenium (Tetrahedron Letters, 1970, No. 5, pp365 or J. Mol. Catal, 1989, pL11), 3) phosphine complexes of ruthenium chloride (unscreened application 52-36617), 4) phosphine complexes of rhodium chloride and palladium chloride (Chem. Lett., 1977, p1495, or Bull. Inst. Chem. Res., Hyoto Univ., 1981, Vol. 59, p88) and 5) phosphine complexes of platinum (J. Chem. Soc., Chem. Commun., 1988, p602).

All of these known methods must use a large amount of solvent for reaction, and thus complicated procedures must be used to separate formic acid as the reaction product, from catalysts and solvents. Further, the reaction rate and the final yield of these methods are not high enough and thus these methods are not necessarily suitable for practical application.

For these reasons, the development of a new applicable method to produce formamide derivatives has an excellent productivity and a fast reaction rate is needed.

As described above in detail, formic acid and its derivatives have a large industrial value and fundamental improvements of the conventional production methods are strongly needed. So far, such improvements have never been reported.

SUMMARY OF THE INVENTION

The present invention was made to solve the above problems of the prior art, and provides a new method to produce formic acid or its derivatives from raw materials of low toxicity with a high reaction rate and featuring ease of operation and a satisfactory productivity.

To attain the above objects, the present invention provides a new method for producing formic acid or derivatives thereof by the reaction of carbon dioxide ($CO_2$) in the super critical state with an active hydrogen group-containing compound.

In the present invention, as described above, carbon dioxide ($CO_2$) in the super critical state react with hydrogen ($H_2$) as an active hydrogen group-containing compound, with an alcoholic compound (ROH), an amine compound ($NR_1R_2R_3$) or a carbamate compound, to produce formic acid, a formic acid ester, a formate, formamide and their derivatives.

BRIEF DESCRIPTION OF THE DRAWINGS

The attached

DETAILED DESCRIPTION OF THE INVENTION

Figure 1:
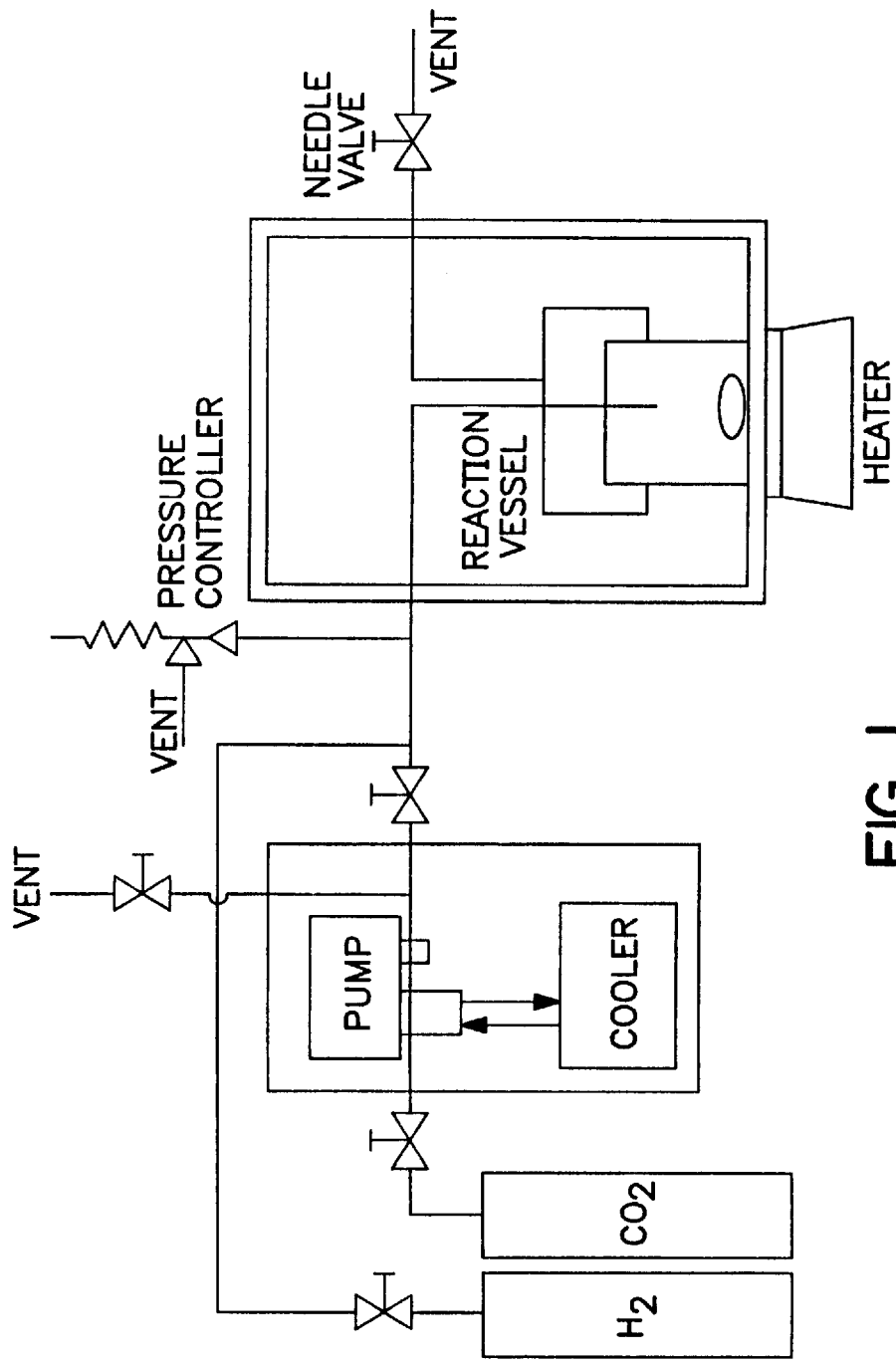
FIG. 1 shows the basic construction of a typical reaction system used in the production method according to the present invention.

The production method according to the present invention is further described below in detail.

The essential feature of the present invention is, as described above, the use of carbon dioxide in the supercritical state (can be expressed as $scCO_2$).

We can not find, in the prior art, a really effective method to produce formic acid or derivatives thereof using carbon dioxide as a raw material. The present invention has realized a new horizon for the provision of an innovative technology replacing the prior art.

The present invention has been made on the general knowledge that, by using carbon dioxide in the supercritical state (expressed as $scCO_2$) in the reaction, the reaction rate remarkably increases and a highly effective production method is realized for formic acid and derivatives thereof. In the methods of the prior art a large amount of organic solvent must be used, and complicated procedures are required to separate the derived formic acid or its derivatives from the solvent. In the present invention, in contrast, these inconveniences do not exist. Because $scCO_2$ is used as the reaction medium, the separation can be carried out by slightly varying the temperature or pressure because of the nature of the supercritical fluids, and as a result, formic acid can be produced without using solvents, which is a significant advantage of the present invention.

In the production method according to the present invention, as described above, carbon dioxide in the super-critical state ($scCO_2$) reacts with an active hydrogen group-containing compound. The active hydrogen group-containing compound in this instance is used in the broader meaning of the term, and generally include those compound whose hydrogen atom is easily dissociated in the scene of reaction with supercritical carbon dioxide, and which has a large reaction activity. This also means that the hydrogen atom has a high dissociation level and a new chemical bond is easily formed in these compounds.

The type of these active hydrogen group-containing compound is not particularly limited, and may include, for example, hydrogen in the molecular state ($H_2$) as well as compounds having a hydrogen group in the bonded state of —O—H, —N—H, —S—H, —C—H, etc. More specifically, an active hydrogen group-containing compound may include compounds having such and active group as hydroxyl, carboxyl, carboxylamide, amino, imino, carbamate, urea, and vinyl group.

Typical examples, respectively, are alcohol, carboxylic acid, carboxylic acid amide, amine, imine, iminoalcohol, carbamate, urea compounds, and vinyl compounds.

By using, for example, hydrogen, an alcohol compound, and an amine or a carbamate as an active hydrogen group-containing compound, we can produce formic acid, a formic acid ester, and formamide derivatives, respectively, in the production method according to the present invention.

The reaction of supercritical carbon dioxide ($scCO_2$) and an active hydrogen group-containing compound is accelerated in the presence of a metal catalyst. The metal catalyst to be used may be a metal, a metal compound, or a metal complex, preferably transition metal, compound or complex of Group VIII transition metal in particular. Among others, complexes of Group VIII metals are useful.

For example, complexes of metals such as rhodium, palladium, ruthenium, iridium or platinum are suitable. These are so-called catalysts or reaction accelerating agents.

Of course, a wide range of other transition metals than above can be used. They include, for example, Ni, Fe, and Co as Group VIII, and Ti, V, Nb, Bi, Sr, Cd, Sn, Ta, Mo, W, Sb, Sm, Ce, Y, Er, Nd, etc. Complexes of these transition metals are also used appropriately.

These are used as a homogeneous or heterogeneous system but should preferably be soluble in $scCO_2$ to enable homogeneous reaction. More specifically, we can use the compound expressed by a generalized formula MXY(Ln) where M is rhodium, palladium, iridium, ruthenium, platinum or other metals. Monovalent metal compounds when these are favorable, may be expressed by a generalized formula MXLn, where X may be halogenoic acid group, carboxylic acid group, carbonate group, hydrogencarbonate group, hydrogen group, etc. Where both X and Y exist, the same or different ones of these groups are used.

The ligands are preferably CO, cyclopentadienyl ligands, organic nitrogen compound ligands, and phosphine ligands $PR^1R^2R^3$ ($R^1$, $R^2$ and $R^3$ may be the same or different. They indicate aliphatic group, alicyclic group or aromatic group, and further indicate phosphine ligands with two ligating atoms. They include, for example, trimethylphosphine, triethylphosphine, tripropylphosphine, tributylphosphine, tricyclohexylphosphine, triphenylphosphine, dimethylphenylphosphine, diphenylmethylphosphine, trifluorophosphine and other tertiary phosphines, trimethylphosphite, tristhylphosphite, tripropylphosphite, tributylphosphite, triphenylphosphite, and other tertiary phosphite, bis-diphenylphosphinoethane, bis-diphenylphosphinomethane, bis-dimethylphosphinoethane, bis-dimethylphosphinomethane, bis-dimethylphosphinopropane, bis-diisopropylphosphinomethane, bis-diisopropylphosphinoethane and other tertiary bidentate or polydentate phosphine compounds). Ruthenium complexes, among others, have a high activity. To be more specific, the complex catalysts to be used in the present invention include, but are not limited to, the following: $RuH_2(MPe_3)_4$, $RuCl_2(PMe_3)_4$, $RuHCl(PMe_3)_4$, $RuH(CH_3COO)(PMe_3)_3$, $RuH(HCOO)(PMe_3)_3$, $RuH_2(PPh_3)_4$, $RuHCl(PPh_3)_4$, $RuH(CH_3COO)(PPh_3)_3$, $RuH_2(PMe_2Ph)_4$, $RuH_2(PMePh_2)_4$, $RuCl_2(PMe_2Ph)_4$, $RuCl_2(PMePh_2)_4$, $[Ru(CO)_2Cl_2]_2$, $[Ru(CO)_2I_2]_2$, $[Ru(CO)_3Cl_2]_2$, $Ru_3(CO)_{12}$, etc. The amount of the above-mentioned Group VIII metal complexes to be used in the present invention is not limited by a maximum or a minimum amount because the method according to the present invention does not use a solvent and depends on the productivity in the production of formic acid or its derivatives. Said amount is specified by the solubility in $scCO_2$, size of autoclave, and economy. The concentration of the catalyst or reaction accelerating agent is 50 to 5000 ppm, preferably 100 to 1000 ppm by weight.

The use of a basic compound or mixture thereof is also effective in the present invention. Preferable basic compound is a nitrogen compound and the salt of the Group I metal in the periodic table. To be more specific, a nitrogen compound should be an amine compound specified by a generalized formula $NR^1R^2R^3$, preferably alkyl groups with preferable substances are mono-, di-, or tri-alkylamines where $R^1$, $R^2$, and $R^3$ are selected from the group comprising ammonia, trimethylamine, triethylamine, tripropylamine, and tributylamine. The nitrogen compound could also be a cyclicamine. Amount of the nitrogen-containing basic substance is not particularly limited, but should preferably be an amount which can be completely dissolved into $scCO_2$ to form a homogeneous phase. The adequate amount is 100 to 100,000 equivalents with respect to the catalyst or reaction accelerating agent, preferably 1,000 to 10,000 equivalents. Group I or II metal salt to be used includes a carbonate. The examples include $Li_2CO_3$, $LiHCO_3$, $Na_2CO_3$, $NaHCO_3$, $K_2CO_3$, $KHCO_3$, $CaCO_3$, $BaCO_3$, and $SrCO_3$, preferably $K_2CO_3$, $Li_2CO_3$, and $NaCO_3$. The metal salt is not soluble in $scCO_2$, and thus any amount is employed, preferably in the 100 to 100,000 equivalents range with respect to the catalyst or reaction accelerating agent.

When producing formic acid by the reaction of supercritical carbon dioxide ($scCO_2$) and hydrogen, the following conditions are employed in order that the reaction takes place preferably with the homogeneous phase in $scCO_2$:

That is, carbon dioxide generally reaches its critical point at 72.9 atm pressure and 31° C. temperature. The supercritical state is realized above this pressure and temperature level. The critical point for a mixture of carbon dioxide and hydrogen gas is estimated from the research by C. Y. Tsang and W. B. Streett, Chem. Eng. Sci., Vol. 36, pp993–1000 (1981). According to their research, carbon dioxide should be in the 75 to 500 atm range, preferably 80 atm to 200 atm. The hydrogen gas pressure should be in the 20 to 150 atm range, preferably 40 to 100 atm. The reaction temperature should be high enough for the reaction system to maintain the supercritical state, preferably between 40° and 120° C.

It is effective to add water or an alcohol compound to the reaction system. The amount should be in the 10 to 10,000 equivalents range for the catalyst or reaction accelerating agent, preferably 10 to 1,000 equivalents. Reaction will take place in either the batch or the continuous method.

An alcohol compound is used as a raw material reaction agent in the production of formic acid ester. In this instance, the type of the alcohol compound is not particularly limited. Typical examples include primary alcohols and secondary alcohols. They may be monohydric or polyhydric alcohols. Specifically, using the expression of ROH, R group may be selected from alkyl, cycloalkyl, phenyl, benzyl or other groups. Typical examples include methyl alcohol, ethyl alcohol, propyl alcohol, isopropyl alcohol, butyl alcohol, pentyl alcohol, hexyl alcohol, cyclohexyl, alcohol, benzyl alcohol, etc. The amount to be used should be sufficient for these substances to be preferably completely dissolved into $scCO_2$ to form a homogeneous phase. The adequate amount is 100 to 100,000 equivalents for the catalyst or reaction accelerating agent, preferably 2,000 to 50,000 equivalents.

The following are the suitable conditions for the reaction:

That is, carbon dioxide generally reaches its critical point at 72.9 atm pressure and 31° C. temperature. The supercritical state is realized above this pressure and temperature level. The critical point for a mixture of carbon dioxide and hydrogen gas is estimated from the research by C. Y. Tsang and W. G. Streett, Chem. Eng. Sci., Vol. 36, pp993–1000 (1961). According to their research, carbon dioxide should be in the 75 to 500 atm range, preferably 80 atm to 210 atm. The hydrogen gas pressure should be in the 20 to 150 atm range, preferably 40 to 100 atm. The reaction temperature should be high enough for the reaction system to maintain the supercritical state, preferably between 40° and 120° C.

The reaction will take place whether the reaction type is the batch or the continuous method. The reaction time depends on the reaction type. For the batch method, the amine salt of the formic acid, the reaction intermediate, presents no problem even if it remains after the reaction because it is easily converted into carbon dioxide, hydrogen, and amine.

When producing a formamide, an amine compound or a carbamate compound must be used as a raw material for reaction.

The amine compound used in the reaction is a primary or secondary amine which can be expressed by the generalized formula of $R^1NH_2$ or $R^2R^3NH$, where $R^1$, $R^2$, and $R^3$ are the same or different groups selected from alkyl groups, cycloalkyl groups and aryl groups of carbon number 1 to 10, respectively, and include cyclic amines as well. Examples include methylamine, ethylamine, propylamine, butylamine, pentylamine, hexylamine, octylamine, cyclopentylamine, cyclohexylamine, benzylamine, phenylethylamine, dimethylamine, diethylamine, dipropylamine, dibutylamine, dipentylamine, dihexylamine, dioxtylamine, dicyclopentylamine, dicyclohexylamine, dibenzylamine, diphenylamine, phenylethylamine, pyperidine, piperazine, etc. These amine compounds easily react with carbon dioxide, and give carbamate compounds which are expressed by the corresponding generalized formula of $(R^1NH_3)(R^1NHCO_2)$ or $(R^2R^3NH_2)(R^2R^3NCO_2)$. In the present invention, the reaction is not affected even when one uses a carbamate corresponding to the above amine compound directly. A carbamate easily decomposes under the reaction condition to give carbon dioxide and the corresponding amine. For this reason, in the case of a compound which tends to easily gasify like dimethylamine, the carbamate may be used as a raw material. The amount of the nitrogen-containing compound is not particularly limited, but is specified by the size of the autoclave. The adequate amount is 100 to 1,000,000 equivalents for the catalyst or a reaction accelerating agent, preferably 1000 to 500,000 equivalents.

The following conditions are preferably used for the reaction:

That is, carbon dioxide generally reaches its critical point at 72.9 atm pressure and 31° C. temperature. The supercritical state is realized above this pressure and temperature level. The critical point for a mixture of carbon dioxide and hydrogen gas is estimated from the research by C. Y. Tsang and W. B. Streett, Chem. Eng. Sci., Vol. 36, pp993–1000 (1981). According to their research, carbon dioxide is in the 75 to 500 atm range, preferably 80 atm to 210 atm. The hydrogen gas pressure is in the 20 to 150 atm range, preferably between 40 and 100 atm. There is however a feature that the reaction takes place even below the critical point if the catalysts are soluble in that state. For example, the reaction takes place at 10 to 60 atm carbon dioxide pressure as shown in the working examples. The reaction temperature should be high enough for the reaction system to maintain the supercritical state, preferably between 40° and 150° C.

The reaction will take place whether the reaction type is the batch or the continuous method. The reaction time depends on the reaction type. When the batch method is employed, 1 to 24 hours are desirable.

Figure 2:
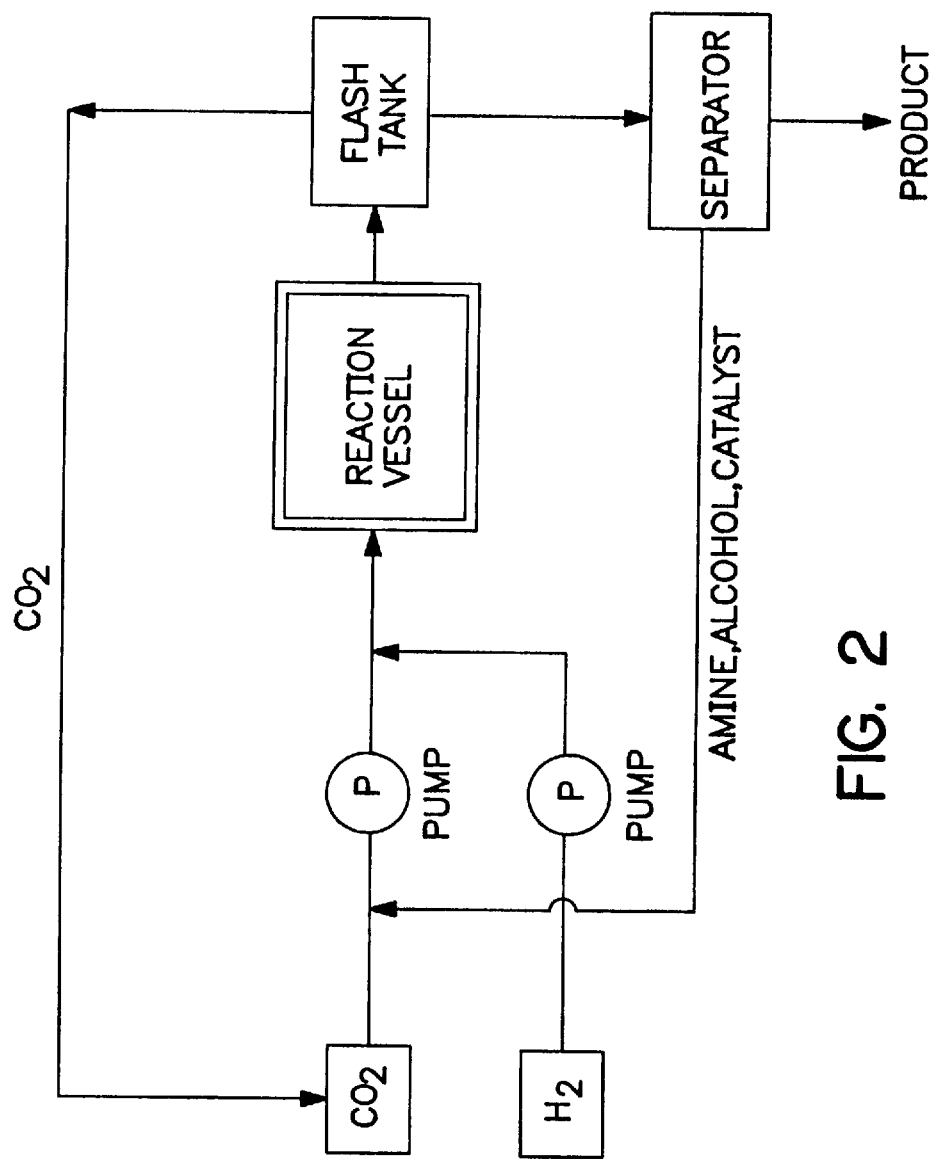
FIG. 2 shows a typical arrangement of a reaction device in a continuous production method according to the present invention.

In any of the above reactions, a reaction device whose basic structure is shown, for example, in FIG. 1 and 2, may be appropriately used.

In FIG. 1, carbon dioxide is cooled and charged to an autoclave. Hydrogen, etc. is also mixed. Then the reaction mixture is set to the supercritical state. When the reaction terminates, the autoclave is cooled, the contents other than hydrogen are liquefied or solidified, and the reaction system is returned to the ordinary temperature and pressure level. FIG. 2 show a typical configuration of a continuous production method according to the present invention. The catalysts, amines, alcohols, etc. are separated and recovered for re-use.

Working examples are shown below to further describe the production method according to the present invention.

EXAMPLES 1 TO 7

Formic acid was produced by reaction in a reaction device shown in FIG. 1.

When the reaction terminated, the autoclave was cooled, the contents in the autoclave other than hydrogen were liquefied or solidified, and the reaction system was returned to the ordinary temperature and pressure level. The yield of derived formic acid was measured by NMR spectroscopy.

As shown in Table 1, Group VIII metal complex (2 to 15 μmol) as the catalysts, triethylamine ($NEt_3$: 5 to 10 mmol) or $K_2CO_3$ (5 mmol) and water (0.1 mmol) were charged into a stainless steel-made autoclave of 50 ml internal volume. Hydrogen gas was set to a specified pressure after argon substitution, and the pressure of carbon dioxide was increased to a specified level. The temperature was raised to the reaction temperature of 50° C. to start reaction. After reaction, the yield of formic acid as the reaction product, was measured by the above-mentioned method. The results are shown in Table 1.

Table 1 shows that formic acid was produced at a high efficiency owing to a far greater reaction velocity than in the Comparative Example to be mentioned later.

TABLE 1

| Test No. | Catalyst (μmol) | $NEt_3$ (mmol) | $P_{CO_2}$ (atm) | $P_{H_2}$ (atm) | Temp (°C.) | Time (hr) | Formic acid/ Catalyst (mole ratio) |
|---|---|---|---|---|---|---|---|
| Example 1 | $RuH_2(PMe_3)_4$ 3.2 | 10 | 124 | 84 | 50 | 10 | 3700 |
| Example 2 | $RuH_2(PMe_3)_4$ 2.5 | 5 | 124 | 84 | 50 | 10 | 2500 |
| Example 3 | $RuCl_2(PMe_3)_4$ 3.2 | 5 | 124 | 84 | 50 | 10 | 2600 |
| Example 4 | $RuCl_2(PMe_3)_4$ 3.4 | 5 | 164 | 34 | 50 | 10 | 160 |
| Example 5 | $RuCl_2(PMe_3)_4$ 2.2 | 5 | 124 | 84 | 50 | 1 | 1040 |
| Example 6 | $RuH_2(PMe_3)_4$ 2.2 | 5 | 124 | 84 | 50 | 1 | 1400 |
| Example 7 | $RuH_2(PMe_3)_4$ 12.2 | $K_2CO_3$ 5 | 125 | 85 | 50 | 15 | 170 |

Comparative Examples 1 to 5

The reaction took place in the condition shown in Table 2.

The reaction rate was smaller than the working examples. The process to separate solvents was complicated.

TABLE 2

| Test No. | Catalyst ($\mu$mol) | solvent | NEt$_3$ (mmol) | Pco$_2$ (atm) | Ph$_2$ (atm) | Temp (°C.) | Time (hr) | Formic acid/ Catalyst (mole ratio) |
|---|---|---|---|---|---|---|---|---|
| Comparative Example 1 | RuCl$_2$(PMe$_3$)$_4$ 2.7 | liquid CO$_2$ | 5 | 125 | 85 | 15 | 15 | 5 |
| Comparative Example 2 | RuH$_2$(PMe$_3$)$_4$ 3.2 | liquid CO$_2$ | 5 | 125 | 85 | 15 | 15 | 21 |
| Comparative Example 3 | RuH$_2$(PMe$_3$)$_4$ 3.0 | THF | 5 | 125 | 85 | 15 | 1 | 80 |
| Comparative Example 4 | RuH$_2$(PMe$_3$)$_4$ 12.2 | THF | K$_2$CO$_3$ 5 | 125 | 85 | 15 | 15 | 140 |
| Comparative Example 5 | RuH$_2$(PMe$_3$)$_4$ 13.2 | scCO$_2$ | 0 | 125 | 87 | 50 | 15 | 0 |

EXAMPLES 8 TO 14

Formic acid was produced by the reaction in the same manner as Working Examples 1 through 7. 5.0 mmol triethylamine was present in the reaction. The reaction was conducted by coexisting water or methanol.

Hydrogen pressure was set in the 75 to 85 atm range so that the total pressure was in the 200 to 215 atm range. Reaction temperature was 50° C., and the volume of the autoclave 50 ml.

The results are shown in Table 3.

As the table shows, the effect of addition of water or alcohol compounds is obvious.

the autoclave were solidified. The reaction system was returned to the ordinary temperature and pressure level. The derived formate compounds were measured by NMR.

Ruthenium trimethyl phosphine complex RuCl$_2$[P(CH$_3$)$_3$]$_4$ (2 to 3 $\mu$mol), triethylamine NEt$_3$ and alcohols were mixed at the ratio shown in Table 4, and charged into a stainless steel-made autoclave of internal volume 50 to 150 ml. Hydrogen gas pressure was increased to the specified level of 80 atm after argon substitution. The carbon dioxide pressure was increased to a specified level to reach the supercritical state and start reaction. After reaction, the

TABLE 3

| Test No. | Catalyst | Amount of catalyst ($\mu$mol) | Additive | Amount of Additive (mmol) | Reaction Time (h) | Formic acid mmol | Formic acid/ catalyst (mole ratio) |
|---|---|---|---|---|---|---|---|
| Example 8 | RuH$_2$[P(CH$_3$)$_3$]$_4$ | 2.2 | none | 0 | 1 | 1.5 | 680 |
| Example 9 | " | 2.2 | H$_2$O | 0.1 | 1 | 3.0 | 1400 |
| Example 10 | " | 2.5 | CH$_3$OH | 13.3 | 1 | 6.2 | 2500 |
| Example 11 | " | 2.9 | H$_2$O | 0.1 | 16 | 4.9 | 1700 |
| Example 12 | " | 2.2 | CH$_3$OH | 13.3 | 14 | 6.0 | 2700 |
| Example 13 | RuCl$_2$[P(CH$_3$)$_3$]$_4$ | 3.2 | H$_2$O | 0.1 | 16 | 8.1 | 2600 |
| Example 14 | " | 2.7 | CH$_3$OH | 13.3 | 15 | 9.1 | 3300 |

EXAMPLES 15 TO 20

Formic acid esters were produced by the reaction in a reaction device shown in FIG. 1.

When the reaction terminated, the autoclave was cooled to the temperature of dry ice-methanol, and the contents in yields of formate compounds, the product, were quantified by the above-mentioned method. The results are shown in Table 4.

The table shows that formic acid esters were produced at a high efficiency owing to a far greater reaction velocity than in the Comparative Example to be mentioned later.

TABLE 4

| Test No. | RuCl$_2$[P(CH$_3$)$_3$]$_4$ ($\mu$mol) | NEt$_3$ (mmol) | R—OH (mmol) | Temp. (°C.) | Time (hr) | Formic acid ester/ catalyst (mole ratio) | Formic acid/ catalyst (mole ratio) |
|---|---|---|---|---|---|---|---|
| Example 15 | 3.4 | 5 | CH$_3$OH 13.3 | 100 | 16 | 150 | 250 |
| Example 16 | 4.2 | 5 | CH$_3$OH 13.3 | 80 | 16 | 330 | 1100 |
| Example 17 | 3.6 | 15.1 | CH$_3$OH 79 | 80 | 60 | 3500 | 4700 |
| Example 18 | 2.9 | 5 | CH$_3$OH 13.3 | 80 | 45 | 560 | 1100 |
| Example 19 | 2.7 | 5 | CH$_3$OH 13.3 | 50 | 15 | 150 | 3300 |

TABLE 4-continued

| Test No. | RuCl$_2$[P(CH$_3$)$_3$]$_4$ (μmol) | NEt$_3$ (mmol) | R—OH (mmol) | Temp. (°C.) | Time (hr) | Formic acid ester/ catalyst (mole ratio) | Formic acid/ catalyst (mole ratio) |
|---|---|---|---|---|---|---|---|
| Example 20 | 2.2 | 5 | C$_2$H$_5$OH 13.7 | 80 | 16 | 200 | 2000 |

Comparative Example 6 to 8

The reactions took place in the conditions shown in Table 5.

It was demonstrated that amines were an essential additive.

TABLE 5

| Test No. | RuCl$_2$[P(CH$_3$)$_3$]$_4$ (μmol) | Additive (mmol) | CH$_3$OH (mmol) | Temp. (°C.) | Time (hr) | Formic acid ester/ catalyst (mole ratio) | Formic acid/ catalyst (mole ratio) |
|---|---|---|---|---|---|---|---|
| Comparative Example 6 | 2.7 | 0 | 79.0 | 80 | 60 | 7 | 0 |
| Comparative Example 7 | 3.2 | -n-Bu$_3$PO 0.72 | 13.3 | 80 | 15 | 7 | 0 |
| Comparative Example 8 | 3.0 | NEt$_3$ 5 | 0 | 50 | 15 | 0 | 2600 |

EXAMPLE 21

The reaction took place in the same manner as in Working Example 15 except that the quantity of the catalyst was 2.7 μmol, and the reaction time 67 hours.

The generation mol ratio of methyl formate as formic acid ester to the catalyst is 910 and the generation mole ratio of formic acid 960.

EXAMPLE 22

The reaction took place in the same manner as in Working Examples 15 to 19 using an autoclave of 300 ml capacity except that the quantity of methanol was 80.0 mmol, that of triethylamine 30.2 mmol, reaction temperature 80° C., and reaction time 64 h.

Generation of methyl formate was 34%. Mole ratio of methylformate to the catalyst was 3500, and the generation mole ratio of formic acid to the catalyst was 6800.

EXAMPLES 23 to 30

Dimethyl formamide was produced by the reaction in a reaction device shown in FIG. 1.

That is, a metal complex and an amine or a carbamate were charged into an autoclave, hydrogen gas was introduced under pressure, and the contents were heated to a specified temperature level. When the temperature stabilized, hydrogen gas was again introduced to a specified pressure level. Carbon dioxide was input under pressure to a specified pressure level to start the reaction. When the reaction terminated, the autoclave was cooled, and the contents other than hydrogen were liquefied or solidified. The reaction system was returned to the ordinary temperature and pressure level. The derived formamide derivatives were measured by NMR and GC. All the reactions proceeded cleanly.

More specifically, as shown in Table 6, RuCl$_2$(P(CH$_3$)$_3$)$_4$ (2.4 to 2.5 μmol) (as Group VIII metal complex) and dimethylamine or the corresponding carbamate were charged into a stainless steel-made autoclave of internal volume 50 to 150 ml. The pressure of hydrogen gas was increased to the specified level of 80 atm after argon substitution. Carbon dioxide was supplied under a 130 atm pressure to start the reaction at the overall pressure of 210 atm. After reaction, the derived DMF was quantified by the above-mentioned method. The results are shown in Table 6. Note that carbamate in Table 6 indicates that of dimethylamine.

Table 6 shows that DMF was produced at a high efficiency with a far greater reaction velocity than in the Comparative Example to be mentioned later. Formic acid was first produced and then disappeared with time giving DMF.

EXAMPLE 31

The reaction took place under the same conditions as in Working Examples 23 to 30 except that the pressure for carbon dioxide was set at 60 atm. The results are shown in Table 6.

EXAMPLE 32

DMF was produced by the reaction of supercritical CO$_2$ at reaction temperature 100° C., hydrogen 80 atm, and carbon dioxide pressure 130 atm using RuCl$_2$[P(CH$_3$)$_3$]$_4$, as the catalyst, and [(CH$_3$)$_2$NH][(CH$_3$)$_2$NCO$_2$]. The results are shown in Table 6. An autoclave of 300 ml capacity was used in the Working Examples 32.

TABLE 6

| Test No. | RuCl$_2$[P(CH$_3$)$_3$]$_4$ ($\mu$mol) | Amine Compounds | Temp. (°C.) | Time (hr) | DMF/catalyst (mole ratio) | Formic acid/ catalyst (mole ratio) |
|---|---|---|---|---|---|---|
| Example 23 | 2.4 | Dimethylamine 1.7 ml | 100 | 20 | 14,500 | 0 |
| Example 24 | 2.4 | Dimethylamine 0.5 ml | 75 | 5 | 1,400 | 2,000 |
| Example 25 | 2.5 | carbamate 35.1 mmol | 100 | 20 | 25,400 | 275 |
| Example 26 | 2.5 | carbamate 87.7 mmol | 100 | 19 | 62,000 | 680 |
| Example 27 | 2.4 | carbamate 212 mmol | 100 | 18 | 156,000 | 4,000 |
| Example 28 | 2.4 | carbamate 280 mmol | 100 | 24 | 188,000 | 113 |
| Example 29 | 2.4 | carbamate 5.0 mmol | 100 | 1 | 2,600 | 3,500 |
| Example 30 | 2.4 | carbamate 5.0 mmol | 100 | 6 | 3,500 | 130 |
| Example 31 | 2.5 | carbamate 5.0 mmol | 100 | 1 | 1,040 | 1,600 |
| Example 32 | 2.7 | carbamate 576.0 mmol | 100 | 37 | 370,000 | trace |

Comparative Examples 9 and 10

The reactions took place in the condition shown in Table 7. The table shows that the presence of a catalyst is essential. It also demonstrates that the reaction activity significantly decreases if THF is sued as a solvent in comparative Example 10.

TABLE 7

| Comparative Example | RuCl$_2$[P(CH$_3$)$_3$]$_4$ ($\mu$mol) | Amine Compounds | Temp. (°C.) | Time (hr) | DMF/catalyst (mole ratio) | HCOOH/Catalyst (mole ratio) |
|---|---|---|---|---|---|---|
| 9 | 0 | carbamate 5 mmol | 100 | 5 | 0 | 0 |
| 10 | 2.4 | carbamate 5 mmol THF Solvent | 100 | 1 | 770 | 390 |

As described above in detail, the present invention allows the production of formic acid and derivatives thereof using less toxic materials and at a higher efficiency owing to the higher reaction velocity. Separation is also easy because no solvents are necessary.

We claim:

1. A method to produce formic acid ester compound by the reaction of carbon dioxide in the supercritical state with hydrogen and an alcohol compound in the presence of a transition metal compound or complex.

2. A method as claimed in claim 1 wherein said reaction takes place in the presence of a basic substance.

3. A method as claimed in claim 1 wherein said reaction takes place in the presence of a Group VIII transition metal compound or complex.

4. A method as claimed in claim 3 wherein said GROUP VIII transition metal is rhodium, palladium, ruthenium, iridium or platinum.

5. A method as claimed in claim 2 wherein said basic substance is a nitrogen-containing organic compound or a salt of Group I metal.

* * * * *